United States Patent
Sorger et al.

(10) Patent No.: US 10,513,611 B2
(45) Date of Patent: *Dec. 24, 2019

(54) METHOD OF SYNTHESIZING NEAR IR, CLOSED CHAIN SULFO-CYANINE DYES

(71) Applicant: Intuitive Surgical Operations, Inc., Sunnyvale, CA (US)

(72) Inventors: Jonathan Sorger, Belmont, CA (US); Jesudoss Koilpillai, Chennai (IN); Veerappan Ramesh, Bhuvanagiri Taluk (IN); Kulandai raj Antony Sekar, Theni (IN); Periyadurai Ratheshkumar, Kottamedu (IN)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/038,095

(22) Filed: Jul. 17, 2018

(65) Prior Publication Data

US 2018/0319987 A1   Nov. 8, 2018

Related U.S. Application Data

(60) Continuation of application No. 15/711,256, filed on Sep. 21, 2017, now Pat. No. 10,053,580, which is a division of application No. 15/204,441, filed on Jul. 7, 2016, now Pat. No. 9,796,854.

(51) Int. Cl.
*C07D 209/14* (2006.01)
*C09B 23/08* (2006.01)
*C09B 23/01* (2006.01)

(52) U.S. Cl.
CPC .......... *C09B 23/086* (2013.01); *C07D 209/14* (2013.01); *C09B 23/0025* (2013.01); *C09B 23/0066* (2013.01)

(58) Field of Classification Search
None
See application file for complete search history.

(56) References Cited

U.S. PATENT DOCUMENTS

| 5,519,145 A | 5/1996 | Fabricius et al. |
| 6,159,657 A | 12/2000 | Fleming et al. |
| 6,887,854 B2 | 5/2005 | Achilefu et al. |
| 9,796,854 B1 | 10/2017 | Sorger et al. |
| 2007/0232805 A1 | 10/2007 | Leung et al. |
| 2017/0127948 A1 | 5/2017 | Sorger |
| 2018/0009987 A1 | 1/2018 | Sorger et al. |

FOREIGN PATENT DOCUMENTS

| WO | WO-0224815 A1 | 3/2002 |
| WO | WO-2007088129 A2 | 8/2007 |

OTHER PUBLICATIONS

Guan, Y. et al., "Improving Therapeutic Potential of Farnesylthiosalicylic Acid: Tumor Specific Delivery via Conjugation with Heptamethine Cyanine Dye," Molecular Pharmaceutics, 2017 [Epub. Mar. 21, 2016], vol. 14 (1), pp. 1-13.

International Search Report and Written Opinion for Application No. PCT/US2017/039491, dated Sep. 29, 2017, 21 pages.

Wu J.B. et al., "Near-Infrared Fluorescence Heptamethine Carbocyanine Dyes Mediate Imaging and Targeted Drug Delivery for Human Brain Tumor," Biomaterials, 67 (2015), pp. 1-10.

Wolinska E., et al., "Near-Infrared Bis(indolium heptamethine cyanine) Dyes with a Spacer Derived from Oligo(ethylene glycol)," Journal of Heterocyclic Chemistry, Sep. 2009, vol. 46, pp. 925-930.

Choi H.S., et al., "Synthesis and In Vivo Fate of Zwitterionic Near-Infrared Fluorophores," Angewandte Chemie International Edition, Jul. 4, 2011, vol. 50, pp. 6258-6263.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Samantha L Shterengarts
(74) *Attorney, Agent, or Firm* — Kilpatrick Townsend & Stockton LLP

(57) ABSTRACT

Compositions and methods of synthesizing near IR, closed chain, sulfo-cyanine dyes are provided.

20 Claims, No Drawings

METHOD OF SYNTHESIZING NEAR IR, CLOSED CHAIN SULFO-CYANINE DYES

CROSS-REFERENCES TO RELATED APPLICATIONS

The present application is a Continuation of U.S. patent application Ser. No. 15/711,256 filed Sep. 21, 2017 (Allowed), which is a Division of Ser. No. 15/204,441 filed Jul. 7, 2016 (now U.S. Pat. No. 9,796,854), the full disclosures which are incorporated herein by reference in their entirety for all purposes.

BACKGROUND OF THE INVENTION

Minimally invasive medical techniques are intended to reduce the amount of tissue that is damaged during diagnostic or surgical procedures, thereby reducing patient recovery time, discomfort, and deleterious side effects. While millions of "open" or traditional surgeries are performed each year in the United States; many of these surgeries can potentially be performed in a minimally invasive manner. One effect of minimally invasive surgery, for example, is reduced post-operative recovery time and related hospital stay. Because the average hospital stay for a standard surgery is typically significantly longer than the average stay for an analogous minimally invasive surgery, increased use of minimally invasive techniques could save millions of dollars in hospital costs each year. While many of the surgeries performed in the United States could potentially be performed in a minimally invasive manner, only a portion currently employ these techniques due to instrument limitations, method limitations, and the additional surgical training involved in mastering the techniques.

Minimally invasive tele-surgical systems are being developed to increase a surgeon's dexterity as well as to allow a surgeon to operate on a patient from a remote location. Telesurgery is a general term for surgical systems where the surgeon uses some form of remote control, e.g., a servomechanism, or the like, to manipulate surgical instrument movements rather than directly holding and moving the instruments by hand. In such a telesurgery system, the surgeon is provided with an image of the surgical site at the remote location. While viewing the surgical site on a suitable viewer or display, the surgeon performs the surgical procedures on the patient by manipulating master control input devices, which in turn control the motion of instruments. These input devices can move the working ends of the surgical instruments with sufficient dexterity to perform intricate surgical tasks.

Minimally invasive medical techniques, including telesurgical systems can be further aided by improving visualization of the tissue where the procedure is to be carried out. One way to improve visualization of tissue is through the use of dyes capable of targeted visualization of tissue. Thus, there is a need for novel methods of preparing dyes capable of targeted visualization of tissue such as near IR, closed chain, sulfo-cyanine dyes. Surprisingly, the present invention meets these and other needs.

BRIEF SUMMARY OF THE INVENTION

The present invention generally provides novel, compositions and methods of preparing near IR, closed chain, sulfo-cyanine dyes.

In a first embodiment, the present invention provides a method of preparing a compound of Formula V:

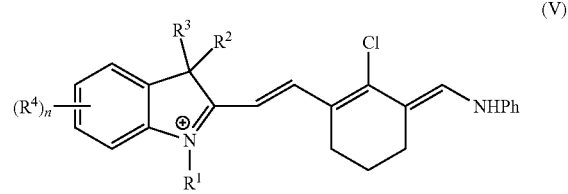

(V)

or salts thereof,
the method comprising:
    forming a reaction mixture comprising a base, a solvent, a compound of Formula I:

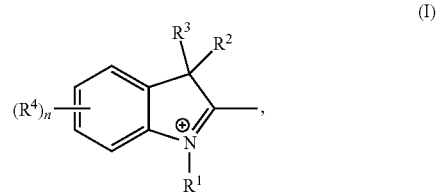

(I)

and
    a compound of Formula II:

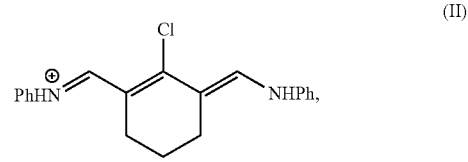

(II)

under conditions suitable to prepare the compound of Formula V having a purity of at least 75%, wherein $R^1$ is $C_{1-6}$ alkylene-$SO_3H$; $R^2$ and $R^3$ are each independently selected from the group consisting of H, $C_{1-6}$ alkyl, $C_{1-6}$ alkylene-$SO_3H$ and $C_{1-6}$ alkylene-COOH; each $R^4$ is independently selected from the group consisting of H, $C_{1-6}$ alkyl, —$SO_3H$, and $C_{1-6}$ alkylene-$SO_3H$; and subscript n is an integer from 0 to 4.

In a second embodiment, the present invention provides a method of preparing a compound of Formula VI:

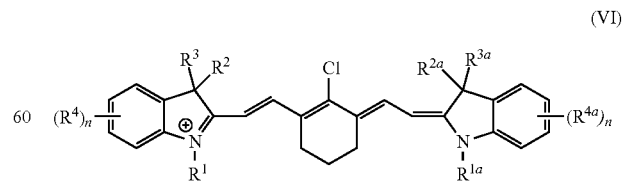

(VI)

or salts thereof, the method comprising: forming a reaction mixture comprising a base, a solvent, a compound of Formula V:

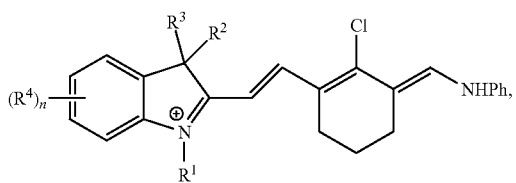

and a compound of Formula III:

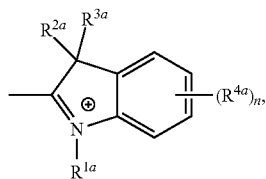

under an inert atmosphere and without exposure to visible light, to prepare the compound of Formula VI, wherein $R^1$ and $R^{1a}$ are each independently $C_{1-6}$ alkylene-$SO_3H$; $R^2$, $R^{2a}$, and $R^3$ are each independently selected from the group consisting of H, $C_{1-6}$ alkyl, and $C_{1-6}$ alkylene-$SO_3H$; $R^{3a}$ is $C_{1-6}$ alkylene-COOH; each $R^4$ and $R^{4a}$ is independently selected from the group consisting of H, $C_{1-6}$ alkyl, —$SO_3H$, and $C_{1-6}$ alkylene-$SO_3H$; and each subscript n is an integer from 0 to 4.

In a third embodiment, the present invention provides a compound having the formula compound of Formula VI:

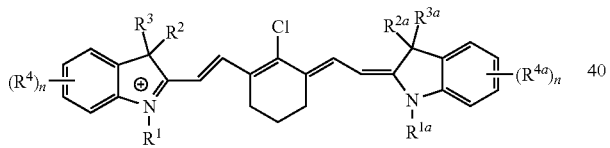

wherein $R^1$ and $R^{1a}$ are each independently $C_{1-6}$ alkylene-$SO_3H$; $R^2$, $R^{2a}$, and $R^3$ are each $C_{1-6}$ alkyl; $R^{3a}$ is $C_{1-6}$ alkylene-COOH; each $R^4$ and $R^{4a}$ is independently selected from the group consisting of H and $C_{1-6}$ alkyl; and each subscript n is an integer from 0 to 4, or salts thereof.

In a forth embodiment, the present invention provides a method of preparing a compound of Formula VII:

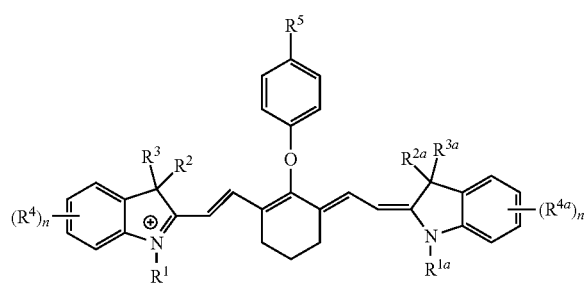

or salts thereof, the method comprising: forming a reaction mixture comprising a base, a solvent, a compound of Formula VI:

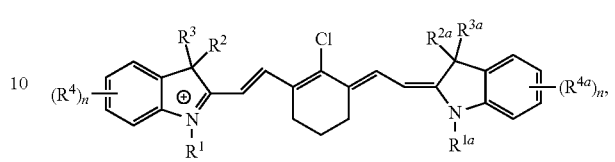

and a compound having the structure:

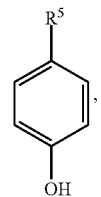

under an inert atmosphere and without exposure to visible light, to prepare the compound of Formula VII, wherein $R^1$ and $R^{1a}$ are each independently $C_{1-6}$ alkylene-$SO_3H$; $R^2$, $R^{2a}$, and $R^3$ are each independently selected from the group consisting of H, $C_{1-6}$ alkyl, and $C_{1-6}$ alkylene-$SO_3H$; $R^{3a}$ is $C_{1-6}$ alkylene-COOH; each $R^4$ and $R^{4a}$ is independently selected from the group consisting of H, $C_{1-6}$ alkyl, —$SO_3H$, and $C_{1-6}$ alkylene-$SO_3H$; $R^5$ is $SO_3H$; and each subscript n is an integer from 0 to 4.

In a fifth embodiment, the present invention provides a compound of Formula VII:

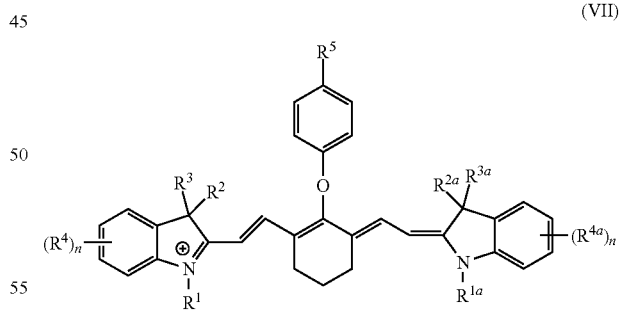

wherein $R^1$ and $R^{1a}$ are each independently $C_{1-6}$ alkylene-$SO_3H$; $R^2$, $R^{2a}$, and $R^3$ are each independently selected from the group consisting of H, $C_{1-6}$ alkyl, and $C_{1-6}$ alkylene-$SO_3H$; $R^{3a}$ is $C_{1-6}$ alkylene-COOH; each $R^4$ and $R^{4a}$ is independently selected from the group consisting of H, $C_{1-6}$ alkyl, —$SO_3H$, and $C_{1-6}$ alkylene-$SO_3H$; $R^5$ is $SO_3H$; and each subscript n is an integer from 0 to 4, or salts thereof.

In a seventh embodiment, the present invention provides a method of preparing a compound of Formula VIII:

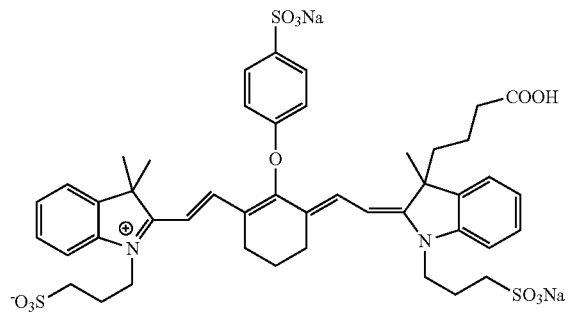
(VIII)

the method comprising: forming a reaction mixture comprising a solvent, sodium acetate and a compound of Formula VII having the structure:

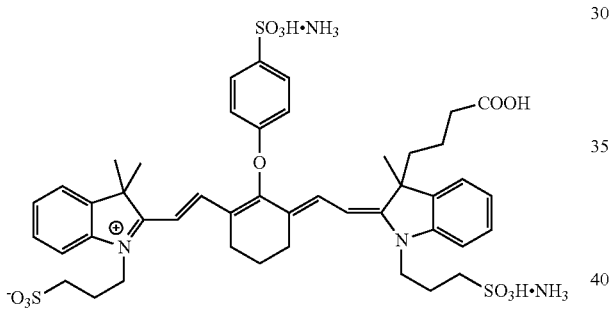

under conditions suitable to form the compound of Formula VIII substantially free of the compound having the structure:

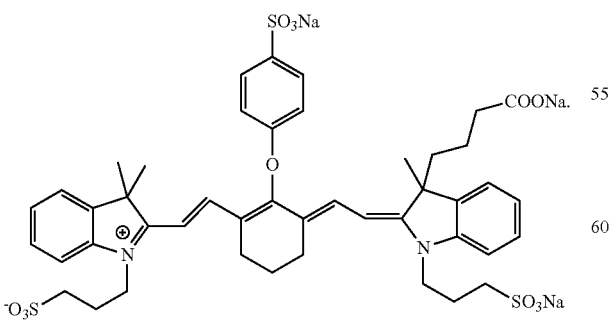

In an eighth embodiment, the present invention provides a compound having the structure:

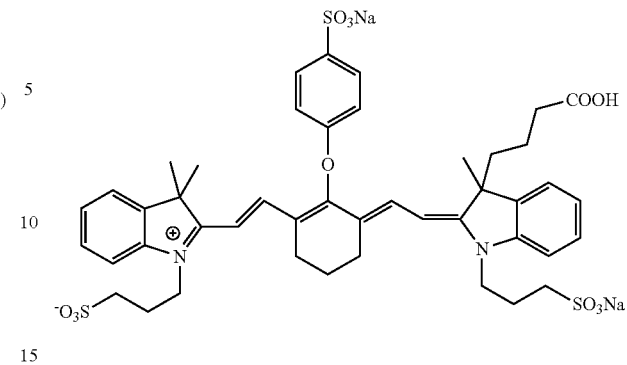

substantially free of the compound having the structure:

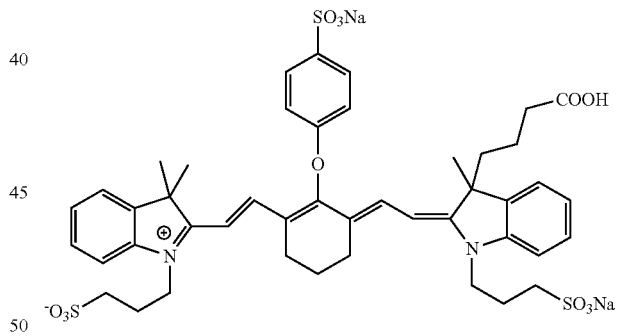

In a ninth embodiment, the present invention provides a method of preparing a compound of Formula VIII having the structure:

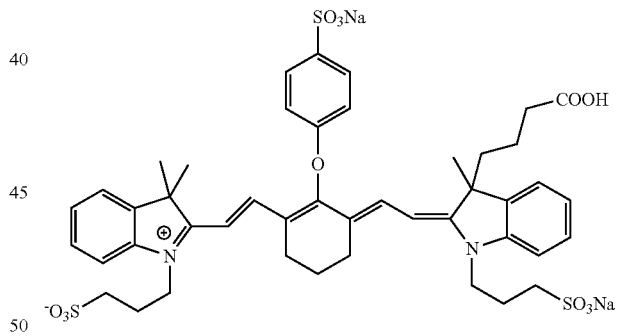

the method comprising:

forming a first reaction mixture comprising triethylamine, methanol, a compound of Formula I having the structure:

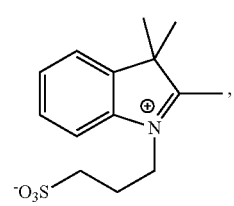

and a compound of Formula II having the structure:

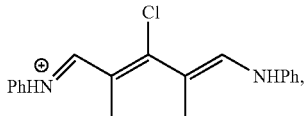

under conditions sufficient to prepare a compound of Formula V having the structure:

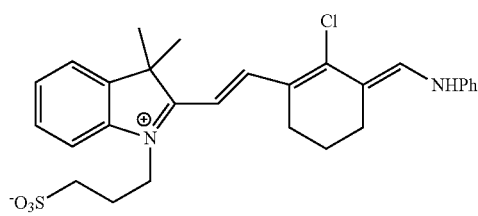

or salts thereof, the compound of Formula V having a purity of at least 95% and substantially free of a compound of Formula IV having the structure:

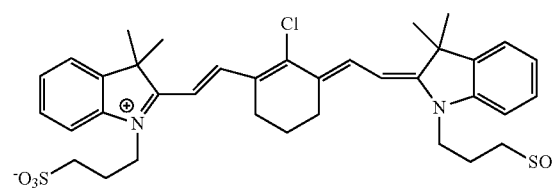

forming a second reaction mixture comprising triethylamine, acetic acid, acetonitrile, the compound of Formula V, and a compound of Formula III having the structure:

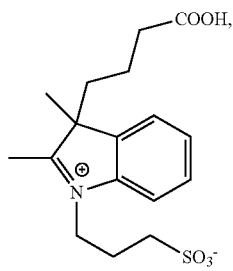

under an Argon atmosphere and without exposure to visible light, to prepare the compound of Formula VI having the structure:

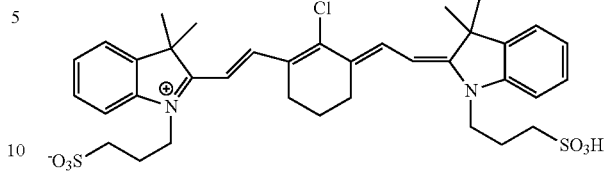

or salts thereof;

forming a third reaction mixture comprising sodium carbonate, dimethylformamide, the compound of Formula VI, and the compound having the structure:

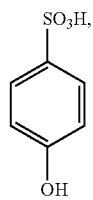

under an inert atmosphere and without exposure to visible light, to prepare the compound of Formula VII having the structure:

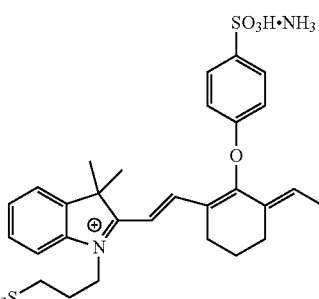

and forming a fourth reaction mixture comprising sodium acetate, the compound of Formula VII, and water, under conditions suitable to form the compound of Formula VIII substantially free of the compound having the structure:

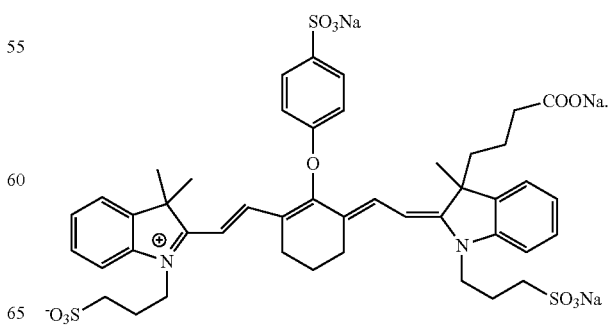

DETAILED DESCRIPTION OF THE INVENTION

I. General

The present invention provides novel compositions and methods for preparing near IR, closed chain, sulfo-cyanine dyes for use in visualizing tissue under illumination with near-infrared radiation. Methods include mono-additions, which allow controlled step-wise condensations to afford the dyes of the present invention.

II. Definitions

"Forming a reaction mixture" refers to the instance of mixing and reacting two or more substances together causing at least one reaction resulting in a chemical transformation or change.

"Base" refers to a substance that can accept protons or any chemical compound that yields hydroxide ions in solution. It is also commonly referred to as any substance that can react with an acid to decrease or neutralize its acidic properties, react with acids to form salts, and promote certain chemical reactions. Examples of bases include non-nucleophilic bases, amine bases, carbonates, halides, phosphates, hydroxides, disilylamides, and hydrides. The base chosen for a particular conversion depends on the nature of the starting materials, the solvent or solvents in which the reaction is conducted, and the temperature at which the reaction is conducted.

"Non-nucleophilic base" refers to a chemical compound that functions as a base with no nucleophilicity. Preferably, the non-nucleophilic base does not react with the other compounds and reagents. A variety of non-nucleophilic bases are known to those of skill in the art. See, e.g., Richard C. Larock, in "Comprehensive Organic Transformation", $2^{nd}$ edition, 1999. In some embodiments, the non-nucleophilic base is a tertiary amine. In one example, the tertiary amine is an aliphatic amine. In some embodiments, the tertiary amine is an aromatic amine. In some embodiments, the tertiary amine is a trialkylamine such as triethylamine or diisopropylethylamine.

"Amine bases" refers to primary, secondary, or tertiary amines, compounds of the formula R'R"R'"N where R', R", and R'" can be hydrogen or organic substituents. Alkylamines where one or more of the substituents is an aliphatic group can be used. Examples include octylamine, dipentylamine, triethylamine, diisopropylamine, and diisopropylethylamine, di-isopropyl ethyl amine, trimethylamine, quinuclidine, and tributylamine. Cycloalkylamines where one or more of the organic substituents is an alicyclic group such as cyclopropyl, cyclopentyl, or cyclooctyl. Monoaryl amines wherein the nitrogen is directly attached to an aromatic ring structure, which can have organic substituents, can also be used. Examples include N,N-methylphenylamine, aniline, and 4-methylaniline. Heterocyclic and substituted heterocyclic amines in which the amine nitrogen is incorporated into a ring structure such as in pyridine, pyrrolidine, and piperidine can also be used. Other examples of amines include imidazole, pyridazine, pyrimidine, and pyrazine and bicyclic amines such as 1,5-Diazabicyclo[4.3.0]non-5-ene (DBN) and 1,8-Diazabicyclo[5.4.0]undec-7-ene (DBU).

Other bases useful in the present invention include carbonate salts such as potassium carbonate, potassium bicarbonate, sodium acetate, sodium carbonate, sodium bicarbonate, and cesium carbonate; halides including cesium fluoride; phosphates such as potassium phosphate, potassium dihydrogen phosphate, and potassium hydrogen phosphate; hydroxides such as lithium hydroxide, sodium hydroxide, and potassium hydroxide; disilylamides such as lithium hexamethyldisilazide, potassium hexamethyldisilazide, and sodium hexamethyldisilazide; and hydrides such as lithium hydride, sodium hydride, and potassium hydride.

"Solvent" refers to polar, aprotic, protic, and non-polar solvents. Examples of solvents include compounds such as hexanes, benzene, toluene, diethyl ether, chloroform, methylene chloride, ethyl acetate, 1,4-dioxane, water, tetrahydrofuran (THF), acetone, acetonitrile, DMF, DMSO, acetic acid, n-butanol, isopropanol, n-propanol, ethanol, methanol, formic acid, carbon tetrachloride, benzenethiol, chlorobenzene, cyclohexanethiol, 1-diethylaminoethanol, ethylene dichloride, ethylene glycol, xylene, 1,1,2,2-tetrachloroethane, phenol, acetic acid, 1-butanol, 2-butanol, 2-butanone, diglyme, dimethylether, dioxane, petroleum ether, N-methyl-2-pyrrolidinone (NMP), heptane, glycerin, HMPA (Hexamethylphosphorus triamide), MTBE (methyl t-butyl ether), nitromethane, pyridine, 1-propanol, 2-propanol, and triethylamine.

"Alkyl" refers to a straight or branched, saturated, aliphatic radical having the number of carbon atoms indicated. For example, $C_1$-$C_6$ alkyl includes, but is not limited to, methyl, ethyl, propyl, isopropyl, butyl, isobutyl, sec-butyl, tert-butyl, pentyl, isopentyl, hexyl, etc. Other alkyl groups include, but are not limited to heptyl, octyl, nonyl, decyl, etc. Alkyl can include any number of carbons, such as 1-2, 1-3, 1-4, 1-5, 1-6, 1-7, 1-8, 1-9, 1-10, 2-3, 2-4, 2-5, 2-6, 3-4, 3-5, 3-6, 4-5, 4-6 and 5-6. The alkyl group is typically monovalent, but can be divalent, such as when the alkyl group links two moieties together.

"Alkylene" refers to an alkyl group, as defined above, linking at least two other groups, i.e., a divalent hydrocarbon radical. The two moieties linked to the alkylene can be linked to the same atom or different atoms of the alkylene. For instance, a straight chain alkylene can be the bivalent radical of —$(CH_2)_n$—, where n is 1, 2, 3, 4, 5 or 6. Alkylene groups include, but are not limited to, methylene, ethylene, propylene, isopropylene, butylene, isobutylene, sec-butylene, pentylene and hexylene. Additionally, alkenylene, alkynylene and cycloalkylene are divalent radicals of alkenyl, alkynyl and cycloalkyl.

"Salts" refers to acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

"Precipitated" and "precipitation" refers to the creation of a solid from a solution. When the reaction occurs in a liquid solution, the solid formed is called the 'precipitate'.

"Inert atmosphere" refers to an atmosphere either containing less than 5,000, in some embodiments, no more than 4,000, or, in yet other embodiments, 400 to 4,000 parts per million of oxygen. In some embodiments, the inert atmosphere contains no more than 1,000, such as 300 to 1,000, parts per million of oxygen. Gases such as nitrogen, argon, carbon dioxide, noble gases, or mixtures thereof are often the major components of the inert atmosphere, although other non-reactive gases may be used. In certain embodiments, argon is employed for this purpose.

"Without exposure to visible light" refers to the absence of light having wavelength(s) between about 400 nm and about 750 nm.

"Substantially free" refers to preferred negative limitations of the compositions of the present invention, and are directed to the amount or concentration of undesired compounds. Generally, the compositions preferably contain less than 5%, preferably less than 2%, more preferably less than 1%, even more preferably less than 0.5%, most preferably zero percent of such undesired compounds by weight of the composition.

III. Methods for Preparing Formula V

As discussed above, there is a need for novel compositions and methods of preparing dyes capable of targeted visualization of tissue such as near IR, closed chain, sulfo-cyanine dyes. The present invention generally provides novel compositions and methods of preparing near IR, closed chain, sulfo-cyanine dyes. As demonstrated below, the mono-addition of compounds of Formula I to compounds of Formula II is an important reaction that allows for a stepwise controlled condensation.

In some embodiments, the present invention provides a method of preparing a compound of Formula V:

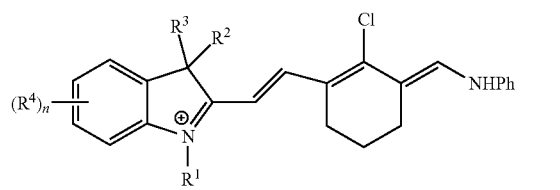

(V)

or salts thereof,
the method comprising:
forming a reaction mixture comprising a base, a solvent, a compound of Formula I:

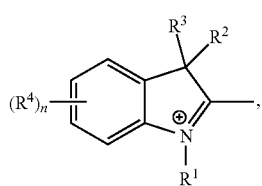

(I)

and
a compound of Formula II:

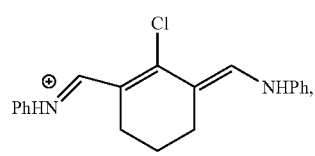

(II)

under conditions suitable to prepare the compound of Formula V having a purity of at least 75%, wherein $R^1$ is $C_{1-6}$ alkylene-$SO_3H$; $R^2$ and $R^3$ are each independently selected from the group consisting of H, $C_{1-6}$ alkyl, $C_{1-6}$ alkylene-$SO_3H$ and $C_{1-6}$ alkylene-COOH; each $R^4$ is independently selected from the group consisting of H, $C_{1-6}$ alkyl, —$SO_3H$, and $C_{1-6}$ alkylene-$SO_3H$; and subscript n is an integer from 0 to 4.

Bases useful in the present invention include non-nucleophilic bases, amine bases, carbonates, halides, phosphates, hydroxides, disilylamides, and hydrides. The base chosen for a particular conversion depends on the nature of the starting materials, the solvent or solvents in which the reaction is conducted, and the temperature at which the reaction is conducted.

A variety of non-nucleophilic bases are useful in the present invention and known to those of skill in the art. See, e.g., Richard C. Larock, in "Comprehensive Organic Transformation," 2nd edition, 1999. In some embodiments, the non-nucleophilic base is a tertiary amine. In some embodiments, the tertiary amine is an aliphatic amine. In some embodiments, the tertiary amine is an aromatic amine. In some embodiments, the tertiary amine is a trialkylamine such as triethylamine or diisopropylethylamine.

Amine bases useful in the present invention include primary, secondary, or tertiary amines, compounds of the formula R'R"R"'N where R', R" and R"' can be hydrogen or organic substituents. Alkylamines where one or more of the substituents is an aliphatic group can be used. Examples include octylamine, dipentylamine, triethylamine, diisopropylamine, and diisopropylethylamine, di-isopropyl ethyl amine, trimethylamine, quinuclidine, and tributylamine. Cycloalkylamines where one or more of the organic substituents is an alicyclic group such as cyclopropyl, cyclopentyl, or cyclooctyl. Monoaryl amines wherein the nitrogen is directly attached to an aromatic ring structure, which can have organic substituents, can also be used. Examples include N,N-methylphenylamine, aniline, and 4-methylaniline. Heterocyclic and substituted heterocyclic amines in which the amine nitrogen is incorporated into a ring structure such as in pyridine, pyrrolidine, and piperidine can also be used. Other examples of amines include imidazole, pyridazine, pyrimidine, and pyrazine and bicyclic amines such as 1,5-Diazabicyclo[4.3.0]non-5-ene (DBN) and 1,8-Diazabicyclo[5.4.0]undec-7-ene (DBU).

In some embodiments, the base is a non-nucleophilic base. In some embodiments, the non-nucleophilic base is selected from the group consisting of triethylamine, di-isopropyl ethyl amine, quinuclidine, pyridine, sodium acetate, sodium carbonate, potassium carbonate and cesium carbonate. In some embodiments, the base is trimethylamine.

Solvents useful in the present invention include polar, aprotic, protic, and non-polar solvents. Examples of solvents useful in the present invention include hexanes, benzene, toluene, diethyl ether, chloroform, methylene chloride, ethyl acetate, 1,4-dioxane, water, tetrahydrofuran (THF), acetone, acetonitrile, DMF, DMSO, acetic acid, n-butanol, isopropanol, n-propanol, ethanol, methanol, formic acid, carbon tetrachloride, benzenethiol, chlorobenzene, cyclohexanethiol, 1-diethylaminoethanol, ethylene dichloride, ethylene glycol, xylene 1,1,2,2-tetrachloroethane, phenol, acetic acid, 1-butanol, 2-butanol, 2-butaone, diglyme, dimethylether, dioxane, petroleum ether, (NMP) N-methyl-2-pyrrolidinone, heptane, glycerin, HMPA (Hexamethylphosphorus triamide), MTBE (methyl t-butyl ether), nitromethane, pyridine, 1-propanol, 2-propanol, and triethylamine.

In some embodiments, the solvent is selected from the group consisting of methanol, ethanol, isopropanol, diethyl ether, acetonitrile, and tetrahydrofuran. In some embodiments, the solvent is methanol.

In some embodiments, the compounds of Formula V are prepared at a purity of at least 70%, 75%, 80%, 85%, 90%, 95%, 96%, 97%, 98% or 99%. In some embodiments, the compound of Formula V is prepared with a purity of at least 90%. In some embodiments, the compound of Formula V is prepared with a purity of at least 95%. In some embodiments, the compound of Formula V is prepared with a purity of at least 98%. In some embodiments, the compound of Formula V is prepared with a purity of at least 98.8%.

In some embodiments, mono-additions allow for controlled step-wise condensations. In some embodiments, the compound of Formula V is prepared with less than 25% of a compound of Formula IV being present:

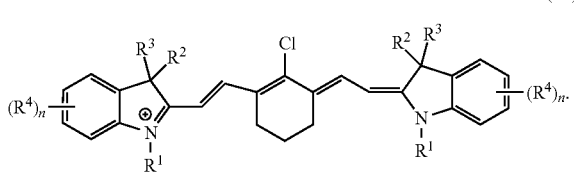
(IV)

In some embodiments, the compound of Formula V is prepared substantially free of the compound of Formula IV.

In some embodiments, the compound of Formula V is prepared in an amount of at least about 10 g. In some embodiments, the compound of Formula V is prepared in an amount of at least about 40 g. In some embodiments, the compound of Formula V is prepared in an amount of at least about 70 g.

In some embodiments, the method comprises: forming the reaction mixture comprising triethylamine and/or methanol, the compound of Formula I having the structure:

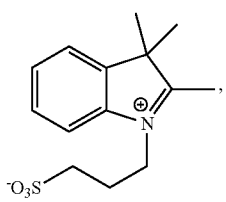

and
the compound of Formula II having the structure:

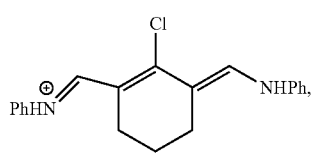

under conditions sufficient to prepare the compound of Formula V having the structure:

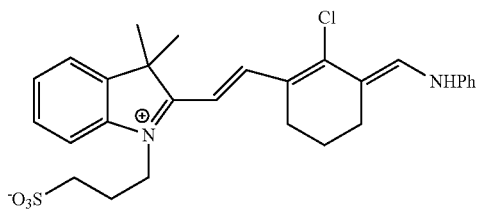

having a purity of at least 95%, substantially free of the compound of Formula IV having the structure:

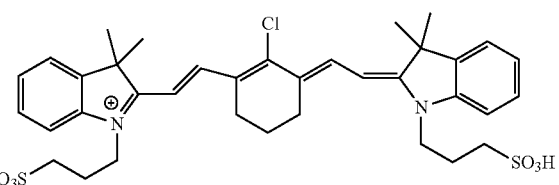

or salts thereof.

The method of preparing the compound of Formula V occurs under suitable reaction conditions. Suitable reaction conditions include all reaction conditions suitable for preparing compounds of Formula V. In some embodiments, reaction conditions include reagents, temperature, pressure, and time. One of skill in the art will appreciate that changes and modifications to the reaction conditions may be practiced within the scope of the appended claims.

The reaction mixtures of the method for preparation of Formula V can be at any suitable temperature. For example, the temperature of the reaction mixture can be of from about 0° C. to about 200° C., such as at about 20, 25, 30, 35, 40, 45, 50, 55, 60, 62, 64, 65, 66, 70, 75 or about 80° C. In some embodiments, the temperature of the reaction mixture can be from about 25° C. to about 75° C., or of from about 40° C. to about 70° C., or of from about 60° C. to about 70° C. In some embodiments, the temperature of the reaction mixture can be about 64° C.

The reaction mixtures for preparation of Formula V of the method can be at any suitable pressure. For example, the reaction mixture can be at atmospheric pressure or above atmospheric pressure. Pressures greater than atmospheric pressure can be achieved by using a pressure vessel and pressurizing with a suitable gas, or using a closed vessel that is then heated. The reaction mixtures can be also be exposed to any suitable environment, such as atmospheric gases, or inert gases such as nitrogen or argon. In some embodiments, the inert gas exposed to the reaction mixture is argon.

The reaction mixtures of the method for preparation of Formula V can also be agitated by any suitable means. For example, the reaction mixtures can be stirred, shaken, vortexed, or others.

Each reaction mixture of the method for preparation of Formula V can be mixed for any suitable period of time from minutes to hours. For example, the reaction mixture can be mixed for about 5 minutes, or 10, 15, 20, 30, 40, 50, 60, 70, 80, 90, 100, 110, or 120 minutes, or for about 3, 4, 6, 12, 16, 24, 36 or 48 hours.

IV. Methods for Preparing Formula VI

The present invention also provides the stepwise addition of compounds of Formula V to compounds of Formula III.

Because compounds of Formula I and Formula III are added to Formula I compounds in different steps, Formula I and Formula III can vary significantly, which allows for a wide variety of compounds of Formula VI.

In some embodiments, the present invention provides a method of preparing a compound of Formula VI:

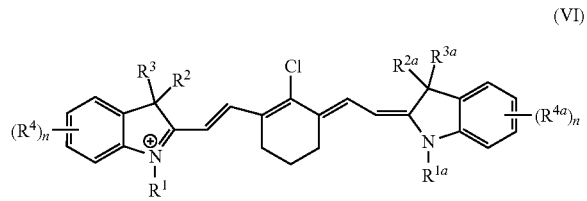

(VI)

or salts thereof,
the method comprising: forming a reaction mixture comprising a base, a solvent, a compound of Formula V:

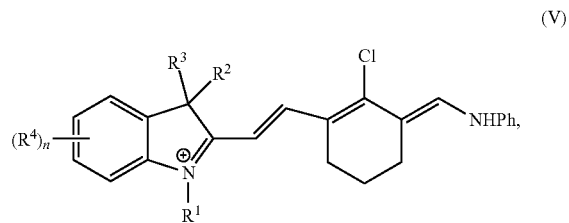

(V)

and
a compound of Formula III:

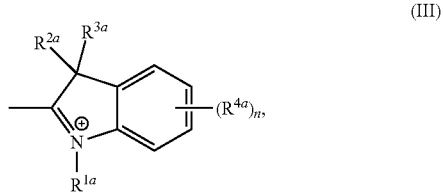

(III)

under an inert atmosphere and without exposure to visible light, to prepare the compound of Formula VI, wherein $R^1$ and $R^{1a}$ are each independently $C_{1-6}$ alkylene-$SO_3H$; $R^2$, $R^{2a}$, and $R^3$ are each independently selected from the group consisting of H, $C_{1-6}$ alkyl, and $C_{1-6}$ alkylene-$SO_3H$; $R^{3a}$ is $C_{1-6}$ alkylene-COOH; each $R^4$ and $R^{4a}$ is independently selected from the group consisting of H, $C_{1-6}$ alkyl, —$SO_3H$, and $C_{1-6}$ alkylene-$SO_3H$; and each subscript n is an integer from 0 to 4.

Bases useful in the present invention include non-nucleophilic bases, amine bases, carbonates, halides, phosphates, hydroxides, disilylamides, and hydrides. The base chosen for a particular conversion depends on the nature of the starting materials, the solvent or solvents in which the reaction is conducted, and the temperature at which the reaction is conducted.

A variety of non-nucleophilic bases are useful in the present invention and known to those of skill in the art. See, e.g., Richard C. Larock, in "Comprehensive Organic Transformation," 2nd edition, 1999. In some embodiments, the non-nucleophilic base is a tertiary amine. In some embodiments, the tertiary amine is an aliphatic amine. In some embodiments, the tertiary amine is an aromatic amine. In some embodiments, the tertiary amine is a trialkylamine such as triethylamine or diisopropylethylamine.

Amine bases useful in the present invention include primary, secondary, or tertiary amines, compounds of the formula where R', R", and R'" can be hydrogen or organic substituents. Alkylamines where one or more of the substituents is an aliphatic group can be used. Examples include octylamine, dipentylamine, triethylamine, diisopropylamine, and diisopropylethylamine, di-isopropyl ethyl amine, trimethylamine, quinuclidine, and tributylamine. Cycloalkylamines where one or more of the organic substituents is an alicyclic group such as cyclopropyl, cyclopentyl, or cyclooctyl. Monoaryl amines wherein the nitrogen is directly attached to an aromatic ring structure, which can have organic substituents, can also be used. Examples include N,N-methylphenylamine, aniline, and 4-methylaniline. Heterocyclic and substituted heterocyclic amines in which the amine nitrogen is incorporated into a ring structure such as in pyridine, pyrrolidine, and piperidine can also be used. Other examples of amines include imidazole, pyridazine, pyrimidine, and pyrazine and bicyclic amines such as 1,5-Diazabicyclo[4.3.0]non-5-ene (DBN) and 1,8-Diazabicyclo[5.4.0]undec-7-ene (DBU).

In some embodiments, the base is a non-nucleophilic base. In some embodiments, the non-nucleophilic base is selected from the group consisting triethylamine, di-isopropyl ethyl amine, quinuclidine, pyridine, sodium acetate, sodium carbonate, potassium carbonate and cesium carbonate. In some embodiments, the base is trimethylamine.

Solvents useful in the present invention include polar, aprotic, protic, and non-polar solvents. Examples of solvents useful in the present invention include hexanes, benzene, toluene, diethyl ether, chloroform, methylene chloride, ethyl acetate, 1,4-dioxane, water, tetrahydrofuran (THF), acetone, acetonitrile, DMF, DMSO, acetic acid, n-butanol, isopropanol, n-propanol, ethanol, methanol, formic acid, carbon tetrachloride, benzenethiol, chlorobenzene, cyclohexanethiol, 1-diethylaminoethanol, ethylene dichloride, ethylene glycol, xylene, 1,1,2,2-tetrachloroethane, phenol, acetic acid, 1-butanol, 2-butanol, 2-butanone, diglyme, dimethylether, dioxane, petroleum ether, N-methyl-2-pyrrolidinone (NMP), heptane, glycerin, HMPA (Hexamethylphosphorus triamide), MTBE (methyl t-butyl ether), nitromethane, pyridine, 1-propanol, 2-propanol, and triethylamine.

In some embodiments, the solvent is selected from the group consisting of acetic acid, methanol, ethanol, isopropanol, diethyl ether, acetonitrile, and THF. In some embodiments, the solvent comprises acetic acid and acetonitrile. In some embodiments, the solvent is acetonitrile.

Inert gases are gases that do not undergo chemical reactions under a set of given conditions. The noble gases often do not react with many substances. Inert gases are used generally to avoid unwanted chemical reactions degrading a sample. These undesirable chemical reactions are often oxidation and hydrolysis reactions with the oxygen and moisture in air. In some embodiments, the inert atmosphere is Argon.

In some embodiments, $R^1$ and $R^{1a}$ are each independently $C_{1-6}$ alkylene-$SO_3H$; $R^2$, $R^{2a}$, and $R^3$ are each $C_{1-6}$ alkyl; $R^{3a}$ is $C_{1-6}$ alkylene-COOH; and each subscript n is 0.

In some embodiments, $R^1$ and $R^{1a}$ are each $C_3$ alkylene-$SO_3H$; $R^2$, $R^{2a}$, and $R^3$ are each $C_{1-2}$ alkyl; $R^{3a}$ is $C_3$ alkylene-COOH; and each subscript n is 0.

In some embodiments, the method comprises: forming the reaction mixture comprising triethylamine, acetic acid, acetonitrile, the compound of Formula V having the structure:

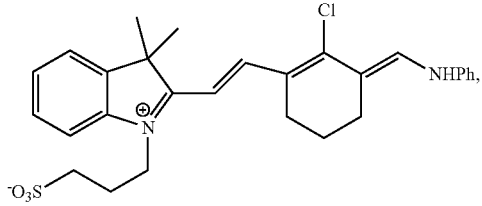

and
the compound of Formula III having the structure:

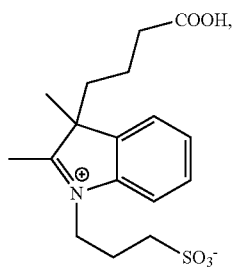

under an Argon atmosphere and without exposure to visible light, to prepare the compound of Formula VI having the structure:

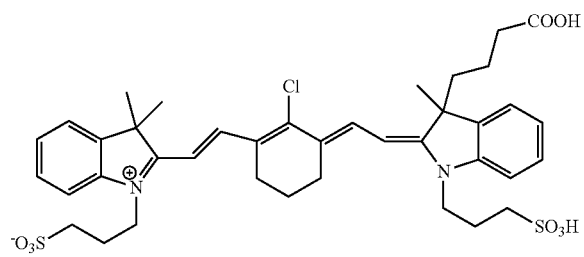

or salts thereof.

In some embodiments, the compound of Formula V is prepared by the method described above.

In some embodiments, the present invention provides a compound having the formula compound of Formula VI:

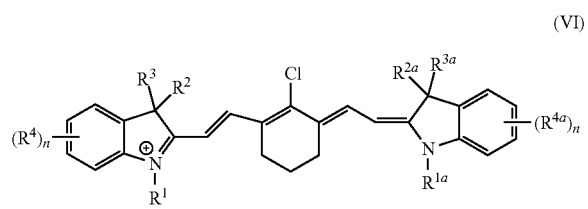

wherein $R^1$ and $R^{1a}$ are each independently $C_{1-6}$ alkylene-$SO_3H$; $R^2$, $R^{2a}$, and $R^3$ are each $C_{1-6}$ alkyl; $R^{3a}$ is $C_{1-6}$ alkylene-COOH; each $R^4$ and $R^{4a}$ is independently selected from the group consisting of H and $C_{1-6}$ alkyl; and each subscript n is an integer from 0 to 4, or salts thereof.

In some embodiments, the compound of Formula VI has the structure:

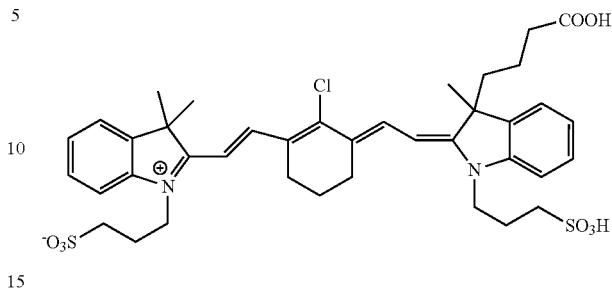

or salts thereof.

The method of preparing the compound of Formula VI occurs under suitable reaction conditions. Suitable reaction conditions include all reaction conditions suitable for preparing compounds of Formula VI. In some embodiments, reaction conditions include reagents, temperature, pressure, and time. One of skill in the art will appreciate that changes and modifications to the reaction conditions may be practiced within the scope of the appended claims.

The reaction mixtures of the method for preparation of Formula VI can be at any suitable temperature. For example, the temperature of the reaction mixture can be of from about 0° C. to about 200° C., such as at about 20, 25, 30, 35, 40, 42, 45, 50, 52, 55, 60, 62, 64, 65, 66, 70, 75 or about 80° C. In some embodiments, the temperature of the reaction mixture can be from about 25° C. to about 75° C., or of from about 30° C. to about 60° C., or of from about 40° C. to about 55° C. In some embodiments, the temperature of the reaction mixture can be about 42° C.

The reaction mixtures for preparation of Formula VI of the method can be at any suitable pressure. For example, the reaction mixture can be at atmospheric pressure or above atmospheric pressure. Pressures greater than atmospheric pressure can be achieved by using a pressure vessel and pressurizing with a suitable gas, or using a closed vessel that is then heated. The reaction mixtures can be also be exposed to any suitable environment, such as atmospheric gases, or inert gases such as nitrogen or argon. In some embodiments, the inert gas exposed to the reaction mixture is argon.

The reaction mixtures of the method for preparation of Formula VI can also be agitated by any suitable means. For example, the reaction mixtures can be stirred, shaken, vortexed, or others.

Each reaction mixture of the method for preparation of Formula VI can be mixed for any suitable period of time from minutes to hours. For example, the reaction mixture can be mixed for about 5 minutes, or 10, 15, 20, 30, 45 or 60 minutes, or for about 1, 2, 3, 4, 6, 12, 16, 24, 36 or 48 hours.

V. Methods for Preparing Formula VII

The present invention provides novel, compositions and methods of preparing near IR, closed chain, sulfo-cyanine dyes. As demonstrated below, compounds of Formula VII are synthesized from compounds of Formula VI.

In some embodiments, the present invention provides a method of preparing a compound of Formula VII:

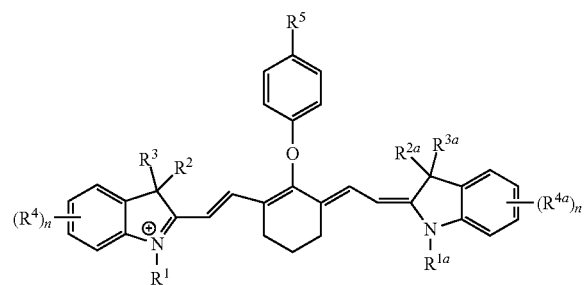
(VII)

or salts thereof, the method comprising: forming a reaction mixture comprising a base, a solvent, a compound of Formula VI:

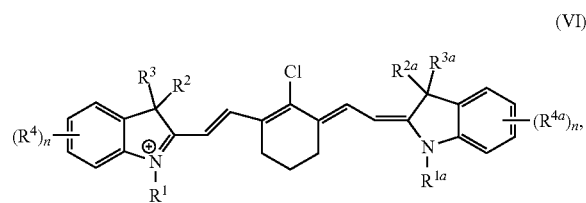
(VI)

and
a compound having the structure:

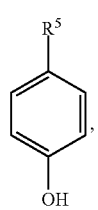

under an inert atmosphere and without exposure to visible light, to prepare the compound of Formula VII, wherein $R^1$ and $R^{1a}$ are each independently $C_{1-6}$ alkylene-$SO_3H$; $R^2$, $R^{2a}$, and $R^3$ are each independently selected from the group consisting of H, $C_{1-6}$ alkyl, and $C_{1-6}$ alkylene-$SO_3H$; $R^{3a}$ is $C_{1-6}$ alkylene-COOH; each $R^4$ and $R^{4a}$ is independently selected from the group consisting of H, $C_{1-6}$ alkyl, —$SO_3H$, and $C_{1-6}$ alkylene-$SO_3H$; $R^5$ is $SO_3H$; and each subscript n is an integer from 0 to 4. In some embodiments, $R^1$ and $R^{1a}$ are each independently $C_{1-6}$ alkylene-$SO_3H$; $R^2$, $R^{2a}$, and $R^3$ are each $C_{1-6}$ alkyl; $R^{3a}$ is $C_{1-6}$ alkylene-COOH; and $R^5$ is $SO_3H$.

Bases useful in the present invention include non-nucleophilic bases, amine bases, carbonates, halides, phosphates, hydroxides, disilylamides, and hydrides. The base chosen for a particular conversion depends on the nature of the starting materials, the solvent or solvents in which the reaction is conducted, and the temperature at which the reaction is conducted.

A variety of non-nucleophilic bases are useful in the present invention and known to those of skill in the art. See, e.g., Richard C. Larock, in "Comprehensive Organic Transformation," 2nd edition, 1999. In some embodiments, the non-nucleophilic base is a tertiary amine. In some embodiments, the tertiary amine is an aliphatic amine. In some embodiments, the tertiary amine is an aromatic amine. In some embodiments, the tertiary amine is a trialkylamine such as triethylamine or diisopropylethylamine.

Amine bases useful in the present invention include primary, secondary, or tertiary amines, compounds of the formula R'R"R"' N where R', R", and R"' can be hydrogen or organic substituents. Alkylamines where one or more of the substituents is an aliphatic group can be used. Examples include octylamine, dipentylamine, triethylamine, diisopropylamine, and diisopropylethylamine, di-isopropyl ethyl amine, trimethylamine, quinuclidine, and tributylamine. Cycloalkylamines where one or more of the organic substituents is an alicyclic group such as cyclopropyl, cyclopentyl, or cyclooctyl. Monoaryl amines wherein the nitrogen is directly attached to an aromatic ring structure, which can have organic substituents, can also be used. Examples include N,N-methylphenylamine, aniline, and 4-methylaniline. Heterocyclic and substituted heterocyclic amines in which the amine nitrogen is incorporated into a ring structure such as in pyridine, pyrrolidine, and piperidine can also be used. Other examples of amines include imidazole, pyridazine, pyrimidine, and pyrazine and bicyclic amines such as 1,5-Diazabicyclo[4.3.0]non-5-ene (DBN) and 1,8-Diazabicyclo[5.4.0]undec-7-ene (DBU).

In some embodiments, the base is a non-nucleophilic base. In some embodiments, the non-nucleophilic base is selected from the group consisting triethylamine, di-isopropyl ethyl amine, quinuclidine, pyridine, sodium acetate, sodium carbonate, potassium carbonate and cesium carbonate. In some embodiments the base is sodium carbonate.

Solvents useful in the present invention include polar, aprotic, protic, and non-polar solvents. Examples of solvents useful in the present invention include hexanes, benzene, toluene, diethyl ether, chloroform, methylene chloride, ethyl acetate, 1,4-dioxane, water, tetrahydrofuran (THF), acetone, acetonitrile, dimethylformamide (DMF), DMSO, acetic acid, n-butanol, isopropanol, n-propanol, ethanol, methanol, formic acid, carbon tetrachloride, benzenethiol, chlorobenzene, cyclohexanethiol, 1-diethylaminoethanol, ethylene dichloride, ethylene glycol, xylene 1,1,2,2-tetrachloroethane, phenol, acetic acid, 1-butanol, 2-butanol, 2-butaone, diglyme, dimethylether, dioxane, petroleum ether, (NMP) N-methyl-2-pyrrolidinone, heptane, glycerin, HMPA (Hexamethylphosphorus triamide), MTBE (methyl t-butyl ether), nitromethane, pyridine, 1-propanol, 2-propanol, and triethylamine.

In some embodiments, the solvent is selected from the group consisting of DMF, acetic acid, methanol, ethanol, isopropanol, diethyl ether, acetonitrile, and tetrahydrofuran. In some embodiments, the solvent comprises acetic acid and acetonitrile. In some embodiments, the solvent comprises DMF.

In some embodiments, the compound of Formula VII is prepared in an amount of at least about 1 g. In some embodiments, the compound of Formula VII is prepared in an amount of at least about 50 g.

In some embodiments, the compound of Formula VII prepared has the structure:

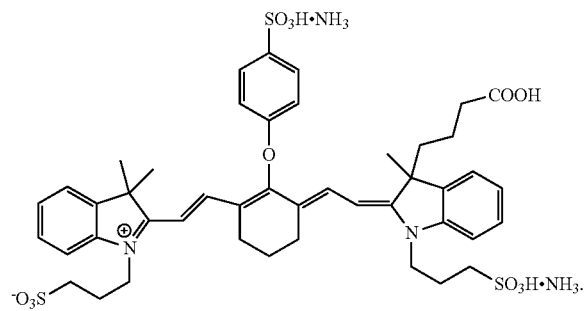

In some embodiments, the compound of Formula VI is prepared by the method described above.

In some embodiments, the method comprises: forming the reaction mixture comprising sodium carbonate, dimethylformamide, the compound of Formula VI having the structure:

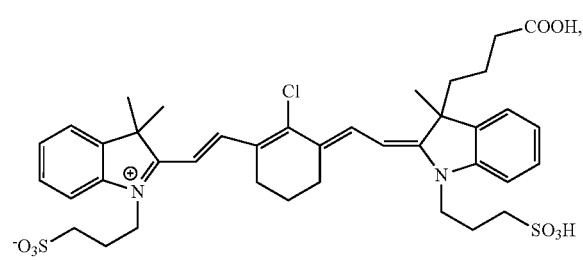

and
the compound having the structure:

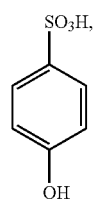 [SMILES: O=S(=O)(O)c1ccc(O)cc1]

under an inert atmosphere and without exposure to visible light, to prepare the compound of Formula VII having the structure:

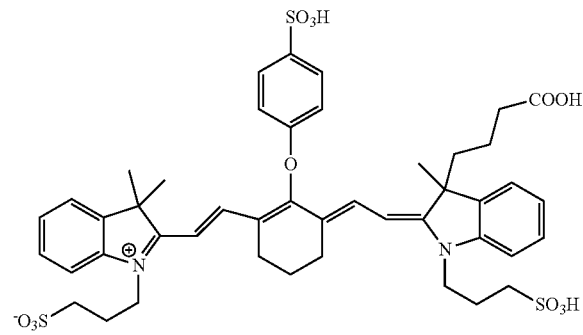

or salts thereof.

In some embodiments, the present invention provides a compound of Formula VII:

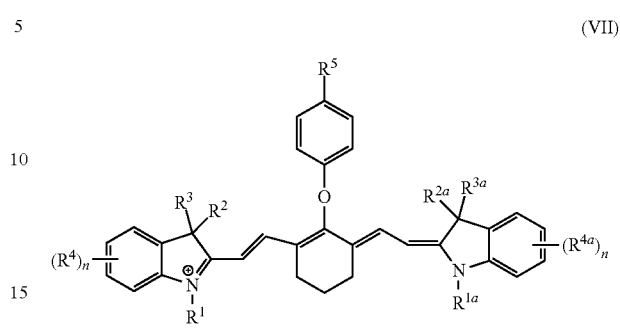

(VII)

wherein $R^1$ and $R^{1a}$ are each independently $C_{1-6}$ alkylene-$SO_3H$; $R^2$, $R^{2a}$, and $R^3$ are each independently selected from the group consisting of H, $C_{1-6}$ alkyl, and $C_{1-6}$ alkylene-$SO_3H$; $R^{3a}$ is $C_{1-6}$ alkylene-COOH; each $R^4$ and $R^{4a}$ is independently selected from the group consisting of H, $C_{1-6}$ alkyl, $-SO_3H$, and $C_{1-6}$ alkylene-$SO_3H$; $R^5$ is $SO_3H$; and each subscript n is an integer from 0 to 4, or salts thereof.

In some embodiments, the compound of Formula VII has the structure:

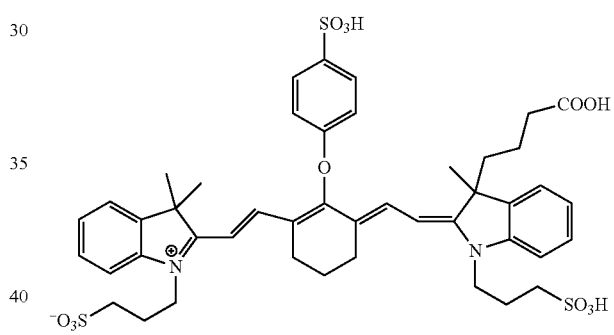

or salts thereof.

In some embodiments, the compound of Formula VII has the structure:

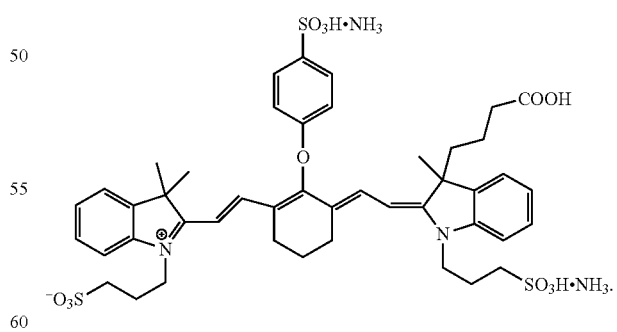

The method of preparing the compound of Formula VII occurs under suitable reaction conditions. Suitable reaction conditions include all reaction conditions suitable for preparing compounds of Formula VII. In some embodiments, reaction conditions include reagents, temperature, pressure, and time. One of skill in the art will appreciate that changes and modifications to the reaction conditions may be practiced within the scope of the appended claims.

The reaction mixtures of the method for preparation of Formula VII can be at any suitable temperature. For example, the temperature of the reaction mixture can be of from about 0° C. to about 200° C., such as at about 20, 25, 30, 35, 40, 45, 50, 55, 60, 62, 64, 65, 66, 70, 75 or about 80° C. In some embodiments, the temperature of the reaction mixture can be from about 25° C. to about 75° C., or of from about 40° C. to about 70° C., or of from about 60° C. to about 70° C. In some embodiments, the temperature of the reaction mixture can be about 62° C.

The reaction mixtures for preparation of Formula VII of the method can be at any suitable pressure. For example, the reaction mixture can be at atmospheric pressure or above atmospheric pressure. Pressures greater than atmospheric pressure can be achieved by using a pressure vessel and pressurizing with a suitable gas, or using a closed vessel that is then heated. The reaction mixtures can be also be exposed to any suitable environment, such as atmospheric gases, or inert gases such as nitrogen or argon. In some embodiments, the inert gas exposed to the reaction mixture is argon.

The reaction mixtures of the method for preparation of Formula VII can also be agitated by any suitable means. For example, the reaction mixtures can be stirred, shaken, vortexed, or others.

Each reaction mixture of the method for preparation of Formula VII can be mixed for any suitable period of time from minutes to hours. For example, the reaction mixture can be mixed for about 5 minutes, or 10, 15, 20, 30, 45 or 60 minutes, or for about 1, 2, 3, 4, 6, 12, 16, 24, 36 or 48 hours.

VI. Methods for Formula VIII

The present invention provides novel, compositions and methods of preparing near IR, closed chain, sulfo-cyanine dyes. As demonstrated below, near IR, closed chain, sulfo-cyanine dyes (compounds of Formula VIII) are synthesized from compounds of Formula VII.

In some embodiments, the present invention provides a method of preparing a compound of Formula VIII:

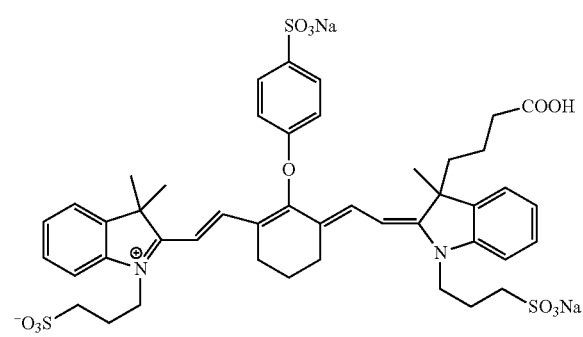

(VIII)

the method comprising: forming a reaction mixture comprising a solvent, sodium acetate and a compound of Formula VII having the structure:

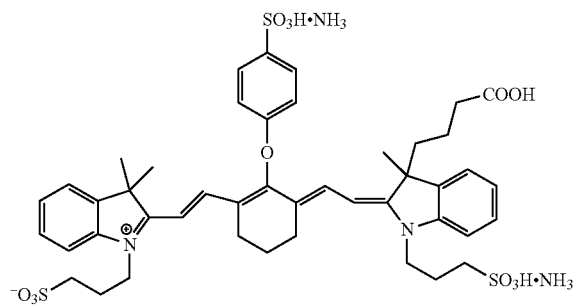

under conditions suitable to form the compound of Formula VIII substantially free of the compound having the structure:

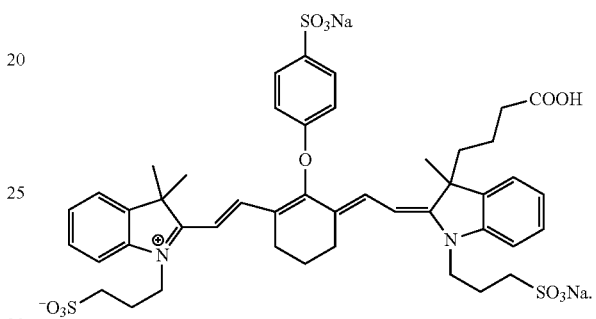

Solvents useful in the present invention include polar, aprotic, protic, and non-polar solvents. Examples of solvents useful in the present invention include hexanes, benzene, toluene, diethyl ether, chloroform, methylene chloride, ethyl acetate, 1,4-dioxane, water, tetrahydrofuran (THF), acetone, acetonitrile, DMF, DMSO, acetic acid, n-butanol, isopropanol, n-propanol, ethanol, methanol, formic acid, carbon tetrachloride, benzenethiol, chlorobenzene, cyclohexanethiol, 1-diethylaminoethanol, ethylene dichloride, ethylene glycol, xylene 1,1,2,2-tetrachloroethane, phenol, acetic acid, 1-butanol, 2-butanol, 2-butaone, diglyme, dimethylether, dioxane, petroleum ether, (NMP) N-methyl-2-pyrrolidinone, heptane, glycerin, HMPA (Hexamethylphosphorus triamide), MTBE (methyl t-butyl ether), nitromethane, pyridine, 1-propanol, 2-propanol, and triethylamine.

In some embodiments, the solvent is selected from the group consisting of water, methanol, ethanol, isopropanol, diethyl ether, tetrahydrofuran, acetonitrile, acetone, ethyl acetate, n-heptane, hexanes and cyclohexane. In some embodiments, the solvent comprises water.

In some embodiments, the method further comprises: washing the reaction mixture with acetonitrile to substantially remove the water.

In some embodiments, the method further comprises: forming a solution of the compound of Formula VIII and methanol; adding the solution to ethyl acetate to precipitate the compound of Formula VIII; washing the precipitated compound of Formula VIII with n-heptane; and heating the precipitated compound of Formula VIII at a temperature of from about 50° C. to about 100° C., thereby forming the compound of Formula VIII having less than 5000 ppm of solvent.

In some embodiments, the compound of Formula VII is prepared by the method described above.

In some embodiments, the compound of Formula VIII has the structure:

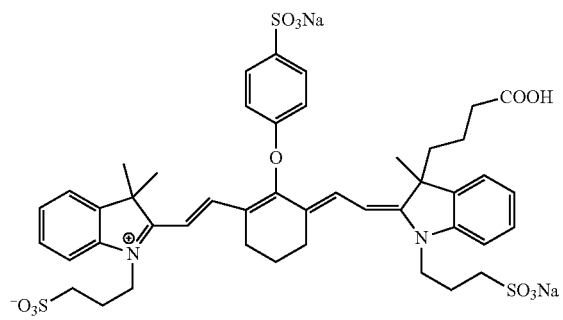

and is substantially free of the compound having the structure:

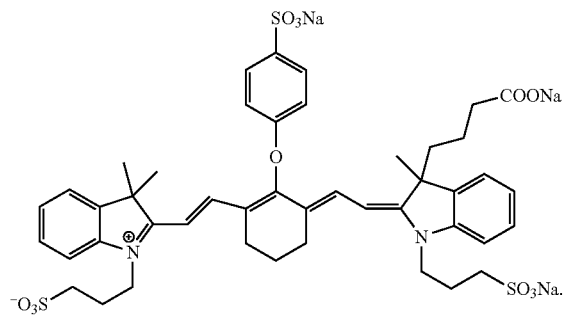

In some embodiments, near IR, closed chain, sulfo-cyanine dyes (compounds of Formula VIII) are synthesized from compounds of Formula I, II, and III. Methods include the mono-addition of compounds of Formula I to compounds of Formula II, an important reaction that allows for a stepwise controlled condensation to produce compounds of Formula V. Subsequent condensation of compounds of Formula V and III allow for a wide variety of compounds of Formula VI. Compounds of Formula VII can then be synthesized from compounds of Formula VI, which in turn can be treated with sodium acetate to afford compounds of Formula VIII.

In some embodiments, the method of preparing a compound of Formula VIII having the structure:

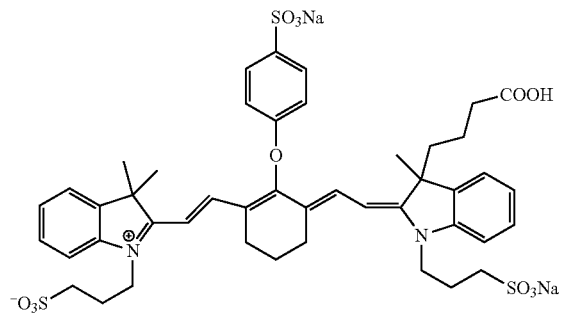

the method comprising:
forming a first reaction mixture comprising triethylamine, methanol, a compound of Formula I having the structure:

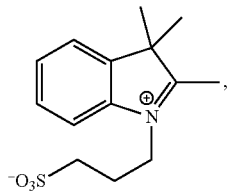

and
a compound of Formula II having the structure:

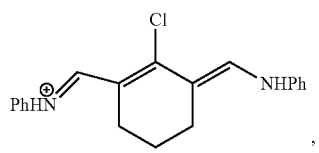

under conditions sufficient to prepare a compound of Formula V having the structure:

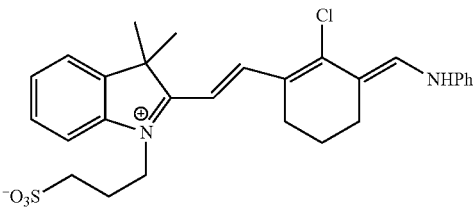

or salts thereof,
the compound of Formula V having a purity of at least 95% and substantially free of a compound of Formula IV having the structure:

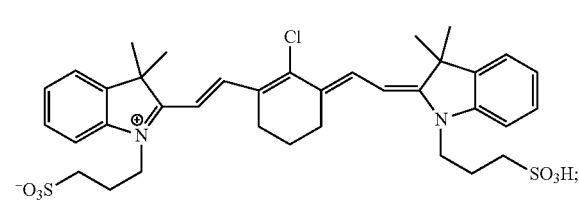

forming a second reaction mixture comprising triethylamine, acetic acid, acetonitrile, the compound of Formula V, and a compound of Formula III having the structure:

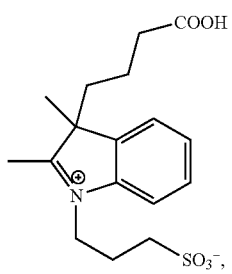

under an Argon atmosphere and without exposure to visible light, to prepare the compound of Formula VI having the structure:

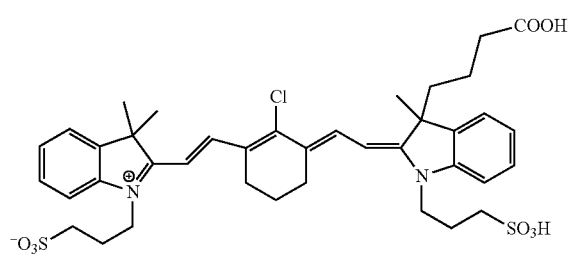

or salts thereof;
forming a third reaction mixture comprising sodium carbonate, dimethylformamide, the compound of Formula VI, and the compound having the structure:

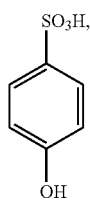 [SMILES: O=S(=O)(O)c1ccc(O)cc1]

under an inert atmosphere and without exposure to visible light, to prepare the compound of Formula VII having the structure:

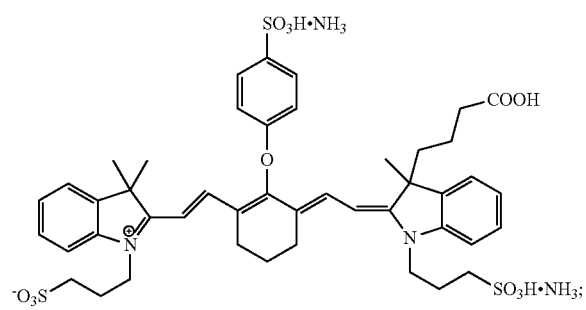

and
forming a fourth reaction mixture comprising sodium acetate, the compound of Formula VII, and water, under conditions suitable to form the compound of Formula VIII substantially free of the compound having the structure:

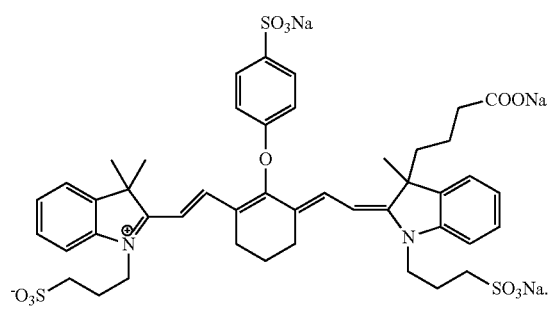

The method of preparing the compound of Formula VIII occurs under suitable reaction conditions. Suitable reaction conditions include all reaction conditions suitable for preparing compounds of Formula VIII. In some embodiments, reaction conditions include reagents, temperature, pressure, and time. One of skill in the art will appreciate that changes and modifications to the reaction conditions may be practiced within the scope of the appended claims.

The reaction mixtures of the method for preparation of Formula VIII can be at any suitable temperature. For example, the temperature of the reaction mixture can be of from about 0° C. to about 200° C., such as at about 0, 5, 10, 15, 20, 22, 25, 27, 30, 35, 40, 45 or about 50° C. In some embodiments, the temperature of the reaction mixture can be from about 10° C. to about 40° C., or of from about 15° C. to about 35° C., or of from about 20° C. to about 30° C. In some embodiments, the temperature of the reaction mixture can be about 25° C.

The reaction mixtures for preparation of Formula VIII of the method can be at any suitable pressure. For example, the reaction mixture can be at atmospheric pressure or above atmospheric pressure. Pressures greater than atmospheric pressure can be achieved by using a pressure vessel and pressurizing with a suitable gas, or using a closed vessel that is then heated. The reaction mixtures can be also be exposed to any suitable environment, such as atmospheric gases, or inert gases such as nitrogen or argon. In some embodiments, the inert gas exposed to the reaction mixture is argon.

The reaction mixtures of the method for preparation of Formula VIII can also be agitated by any suitable means. For example, the reaction mixtures can be stirred, shaken, vortexed, or others.

Each reaction mixture of the method for preparation of Formula VIII can be mixed for any suitable period of time from minutes to hours. For example, the reaction mixture can be mixed for about 5 minutes, or 10, 15, 20, 30, 40, 50, 60, 70, 80, 90, 100, 110, or 120 minutes, or for about 3, 4, 6, 12, 16, 24, 36 or 48 hours.

VII. Examples

Example 1. Synthesis of Formula V Compound (Stage 5)

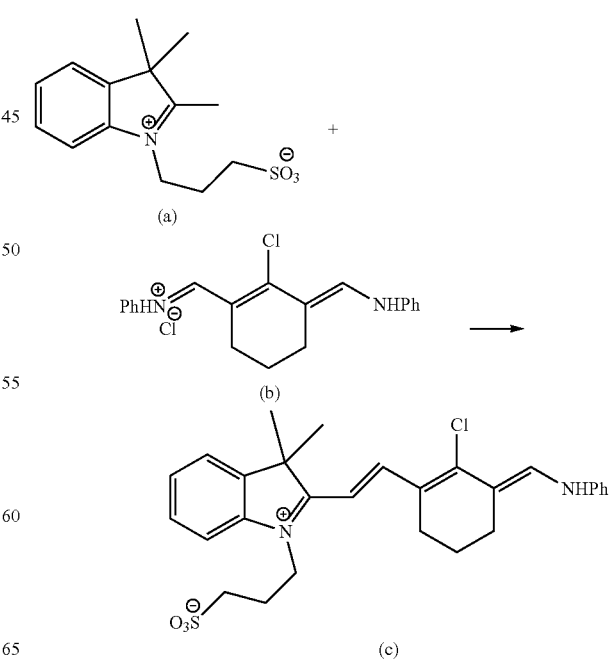

Charge Methanol (1250 ml) into a 3 L RB Flask under argon atmosphere. Charge compound a (50 g) into the above RB flask under argon atmosphere. Stir the mass for 10±5 min at 27±3° C. Charge compound b (76.61 g) into the above reaction mass at 27±3° C. Charge triethylamine (21.57 g) into the above reaction mass at 27±6° C. Heat the reaction mass to 64±2° C. and maintain for 90±10 min at 64±2° C.

When the reaction is complete, cool the reaction mass to 43±2° C. and distil off methanol from the reaction mass to 625±10 mm under vacuum. Cool the reaction mass to 12±2° C. and stir for 1 hr±15 min. Filter the product and wash the product using ethyl acetate (750 ml). Suck dry and unload the product and weight it. Wet weight: 49.1 g Charge Methanol (300 ml) in the 1 lit RB flask. Charge wet solid into the above RB flask. Heat the mass to 66±3° C. and maintain for 15±5 min. Cool the mass to 25±2° C. and stir for 1 hr. Filter the product and wash the product using ethyl acetate (500 ml). Suck dry and unload the product and weight it. [Wet weight: 44.0 g]. Charge Methanol (300 ml) in the 1 lit RB flask. Charge wet solid into the above RB flask. Heat the mass to 66±3° C. and maintain for 15±5 min. Cool the mass to 25±2° C. and stir for 1 hr. Filter the product and wash the product using ethyl acetate (500 ml). Dry the product under vacuum at 40±2° C. for 6 hr. Weight: 42.0 g (Yield: 46.2%). Purity: 98.8%. $^1$H NMR (DMSO-d$^6$, ppm): δ 1.70 (s, 6H), 4.55 (t, 2H), 2.07 (m, 2H), 2.58 (t, 2H), 7.72 (d, 2H), 7.51 (t, 1H), 7.15 (t, 1H), 6.80 (d, 1H), 8.45 (d, 1H), 2.68 (t, 2H), 1.85 (m, 2H), 2.75 (t, 2H), 8.19 (s, 1H), 10.18 (s, 1H), 7.42 (d, 5H).

Example 2. Synthesis of Formula VI Compound
(Stage 6)

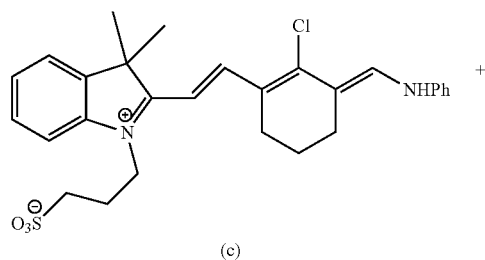

(c)

+

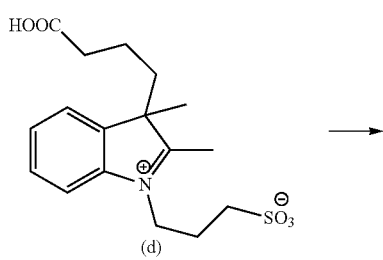

(d)

→

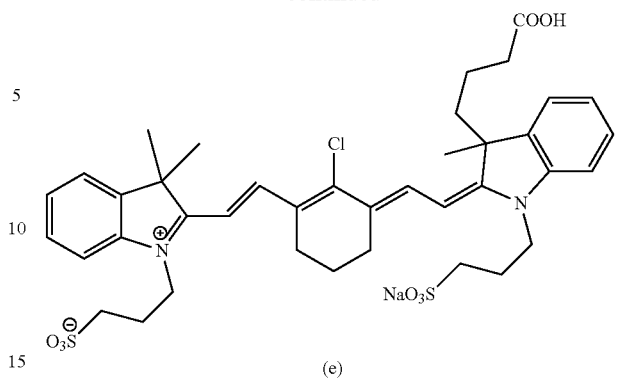

(e)

Note: Degas the acetonitrile, acetic acid and triethyl amine with argon individually for 1 hr at 25±2° C. Compounds of these types are reported to undergo oxidative cleavage with oxygen in presence of light. So oxygen and light should be excluded during the reaction. Charge acetonitrile (380 ml) into a 1000 ml RB flask under dark and argon atmosphere. Purge acetonitrile with argon gas and continue the argon purging throughout the reaction. Charge compound c (38.0 g) into the above RB flask at 27±3° C. Charge acetic acid (152 ml) into the above reaction mass at 27±3° C. Heat the reaction mass to 52±3° C. Charge compound d (28.0 g) into the above reaction mass at 52±3° C. Charge triethyl amine (38.0 g) into the above reaction mass at 52±3° C. Cool the reaction mass to 42±3° C. over the period of 40±5 min. Stir the reaction mass for 3 hr at 42±3° C. Charge slowly diisopropyl ether (1900 ml) into the above reaction mass at 27±3° C. over the period of 30±10 min. Stir the reaction mass for 30±10 min at 27±3° C. Stop the stirring and settle for 30 min. Decant the diisopropyl ether from the mass. Charge methanol (190 ml) into the above mass and stir for 20±5 min at 27±3° C. Charge ethyl acetate (11400 ml) into a 20 L RB flask. Charge slowly the methanol solution of the crude material into above RB flask over the period of 40±10 min at 27±3° C. Stir the mass for 40±10 min at 27±3° C. Filter the mass under nitrogen atmosphere and wash the product with ethyl acetate (304 ml). Unload the product and dry the product under vacuum at 40±3° C. for 6 hr. Weight: 65.0 g (Yield: 94.13%). Purity: 80.2%. $^1$H NMR (DMSO-d$^6$, ppm): δ 1.68 (s, 6H), 1.65 (s, 3H), 2.75 (t, 4H), 6.54 (m, 6H), 4.40 (t, 4H), 6.57 (d, 2H), 8.26 (dd, 2H), 2.59 (t, 4H), 2.25 (m, 2H), 1.85 (t, 2H), 0.7-1.1 (d, 2H), 7.2-7.6 (m, 8H), 1.1-1.2 (t, 9H), 3.0-3.1 (q, 6H).

Example 3. Synthesis of Formula VII Compound (Stage 7)

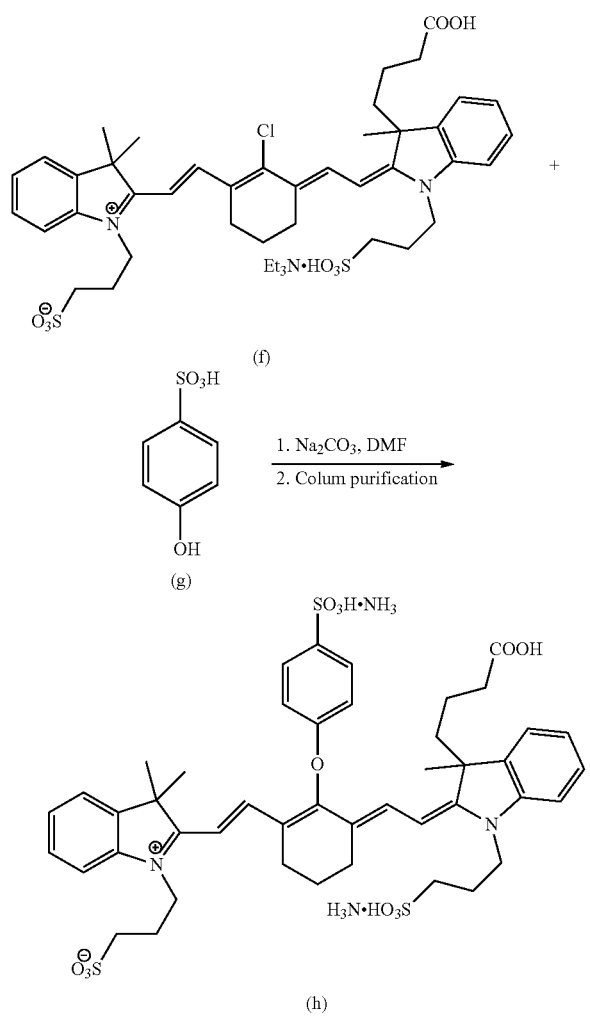

Charge DMF (1400 ml) into a 3 L RB flask under argon atmosphere. Purge DMF with argon for 1 hr. Charge 4-hydroxybenzenesulfonic acid hydrate (122.92 g) into the above RB flask under argon atmosphere. Charge sodium carbonate (112.14 g) into the above reaction mass at 27±3° C. Stir the mass for 15±5 min at 27±3° C. Charge compound f (140 g) into the above reaction mass at 27±3° C. Heat the reaction mass to 62±2° C. and maintain for 2 hrs at 62±2° C.

Cool the reaction mass to 40±2° C. Filter the mass through Buckner funnel and wash the solid using DMF (280 ml). Charge the filtrate slowly into acetone (2520 ml) over a period of 40±5 min. Stir the mass for 40±5 min. Filter the product and wash the product using acetone (560 ml). Unload the wet material in double poly bag.

Charge acetone (2100 ml) into a 5 L RB flask. Charge the wet material into the above RB flask. Stir the mass for 1 hr±10 min at 27±3° C. Filter the product and wash the product using acetone (280 ml). Dry the product under vacuum at 40±2° C. for 6 hr. Crude weight: 180.0 g. Charge methanol (1800 ml) into a 5 L RB flask. Charge the crude material into the above RB flask under stirring. Stir the mass for 15±5 min. Charge silica gel (230-400 mesh) (540 g) into the above RB flask. Stir the mass for 15±5 min. Concentrate the mass under vacuum (250-10 mbar) at 42±3° C. till no more methanol distils off from the mass. Apply high vacuum and remove the final traces of methanol at 42±3° C. Dry the material under high vacuum at 42±3° C. for 4 hrs. Weight: 790 g. Charge silica gel (230-400 mesh, 1800 g) into 10 L beaker.

Charge chloroform (5000 ml) into the above beaker and stir for 10 min. Charge the silica gel slurry into the 10 kg column. Note: Allow the slurry to settle for 12 hrs. Charge the crude compound h slurry into the above column slowly. Column eluted with 16920 ml solvent mixture of $CHCl_3$:MeOH:Aq.$NH_3$ (8.0:1.9:0.1). Note: Collected fractions to be checked for presence of product by TLC. Spot the fractions directly in the TLC plate against the crude material and elute with a mixture of $CHCl_3$:MeOH:aq. $NH_3$=6.0:3.8:0.2. Non polar impurities were observed in the fraction. Column eluted with 112500 ml of solvent mixture of $CHCl_3$:MeOH:Aq.$NH_3$ (7.0:2.85:0.15). Note: Non polar impurities were observed in the fraction. Column eluted with 46340 ml of solvent mixture of $CHCl_3$:MeOH:Aq.$NH_3$ (6.7:3.1:0.2). Note: Non polar impurities were observed in the fraction. Column eluted with 11250 ml of solvent mixture of $CHCl_3$:MeOH:Aq.$NH_3$ (6.5:3.3:0.2). Note: Non polar impurities were observed in the fraction. Column eluted with 90000 ml of solvent mixture of $CHCl_3$:MeOH:Aq.$NH_3$ (6.3:3.5:0.2). Column eluted with 135000 ml of solvent mixture of $CHCl_3$:MeOH:Aq.$NH_3$ (6.0:3.8:0.2) and collected as seven fractions. Take 200 ml from each fraction and concentrate each fraction separately under vacuum at 42±3° C. to the mass volume about 1 ml. Submit the sample of each fraction for HPLC analysis. Combine the fraction having HPLC purity greater than 94.0%. Concentrate the mass completely under high vacuum at 42±3° C. Charge methanol (300 ml) into the above mass and stir for 10±5 min. Charge ethyl acetate (3000 ml) into a 5 L RB flask. Charge methanol solution into the above RB flask containing ethyl acetate, slowly over a period of 20±5 min. Stir the mass for 1 hr±10 min. Filter the product and wash the product using ethyl acetate (200 ml). Dry the product under high vacuum at 50±5° C. for 6 hrs. Weight: 50.34 g (Yield: 33.29%). Purity: 95.54%. $^1$H NMR (DMSO-$d^6$, ppm): δ 1.26-1.37 (s, 9H), 4.26-4.34 (dd, 4H), 1.86-2.03 (m, 8H), 2.74-2.76 (dd, 4H), 1.64-1.71 (t, 2H), 0.45-0.73 (d, 2H), 2.53-2.57 (t, 4H), 7.7-7.86 (dd, 2H), 6.36-6.45 (t, 2H), 7.16-7.52 (m, 8H), 7.11-7.13 (d, 2H), 7.63-7.66 (d, 2H).

Example 4. Synthesis of Formula VIII Compound (Stage 8)

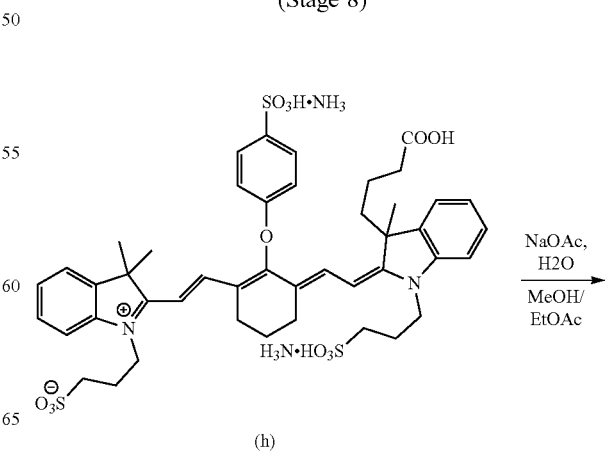

-continued

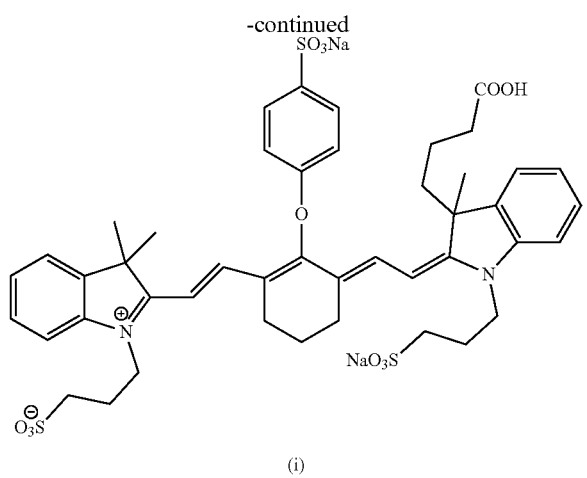

(i)

Charge millipore water (125 ml) into a 1 L RB Flask. Charge compound h (25 g) into the above RB Flask. Stir the mass for 15±5 min at 27±2° C. Charge anhydrous sodium acetate (4.13 g) into the above reaction at 27±3° C. in three lots. Stir the reaction mass for 15±5 min at 27±3° C. Charge acetonitrile (750 ml) into the above reaction mass at 25±3° C. over the period of 20±5 min. Stir the reaction mass for 15±5 min. Stop stirring and settle for 15±5 min. Decant the acetonitrile and collect separately. Charge acetonitrile (125 ml) and stir for 10±5 min. Decant the acetonitrile and collect separately. Charge acetonitrile (125 ml) and stir for 10±5 min. Decant the acetonitrile and collect separately. Submit the sticky mass for HPLC analysis. Limit: HPLC purity should be NLT 97.5% (area). If IPC does not comply, charge millipore water (125 ml) into the above sticky mass and charge acetonitrile (750 ml) into the above reaction mass at 25±3° C. over the period of 20±5 min. Stir the reaction mass for 15±5 min. Stop stirring and settle for 15±5 min. Decant the acetonitrile and collect separately. Charge acetonitrile (125 ml) and stir for 10±5 min. Decant the acetonitrile and collect separately. Charge acetonitrile (125 ml) and stir for 10±5 min. Decant the acetonitrile and collect separately. Submit the sticky mass for HPLC analysis. Repeat these operations until a HPLC purity NLT 97.5% is achieved. If complies, charge methanol (125 ml) into the sticky mass and stir for 10±5 min. Charge ethyl acetate (1250 ml) into a 3 L RB Flask. Charge methanol mass into the above RB flask over a period of 20±5 min. Stir the mass for 2 hr±10 min at 27±3° C. Filter the product and wash the product using n-heptane (2*125 ml) Unload the material and weigh it. Wet weight: 50 g.

Charge n-heptane (250 ml) into the 500 ml RB flask. Charge the wet solid into the above RB flask. Stir the mass for 1 hr±10 min at 27±3° C. Filter the product and wash the product using n-heptane (2*50 ml). Dry the product under high vacuum at 85±5° C. for 12 hrs. Weight: 17.4 g (Yield 68.9%). Purity: 97.74%. $^1$H NMR (CD$_3$OD, ppm): δ 1.3-1.33 (s, 6H), 1.37 (s, 3H), 2.94-2.98 (t, 4H), 2.16-2.26 (m, 4H), 4.3-4.35 (t, 4H), 6.33-6.40 (dd, 2H), 7.90-7.99 (dd, 2H), 2.78-2.82 (t, 4H), 2.0-2.08 (m, 2H), 1.74-1.84 (m, 1H), 1.74-1.85 (m, 1H), 0.65-1.08 (br, 2H), 1.89-1.94 (m, 2H), 7.17-7.89 (m, 12H).

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A compound of Formula VI:

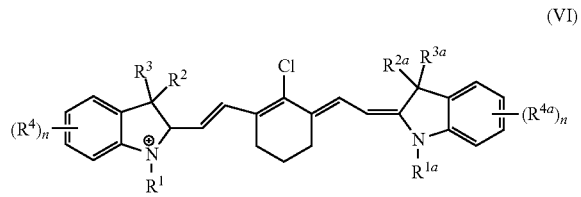

(VI)

wherein $R^1$ and $R^{1a}$ are each independently $C_{1-6}$ alkylene-SO$_3$H;

$R^2$, $R^{2a}$, and $R^3$ are each $C_{1-6}$ alkyl;

$R^{3a}$ is $C_{1-6}$ alkylene-COOH;

each $R^4$ and $R^{4a}$ is independently selected from the group consisting of H and $C_{1-6}$ alkyl; and each subscript n is an integer from 0 to 4, or salts thereof.

2. The compound of claim 1 having a purity of at least 70%.

3. The compound of claim 1 having a purity of at least 80%.

4. The compound of claim 1 having a purity of at least 85%.

5. The compound of claim 1, wherein the compound of Formula VI has the structure:

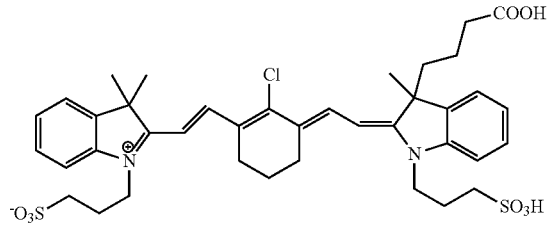

or salts thereof.

6. The compound of claim 5 having a purity of at least 70%.

7. The compound of claim 5 having a purity of at least 75%.

8. The compound of claim 5 having a purity of at least 80%.

9. The compound of claim 5 having a purity of at least 85%.

10. A compound of Formula VII:

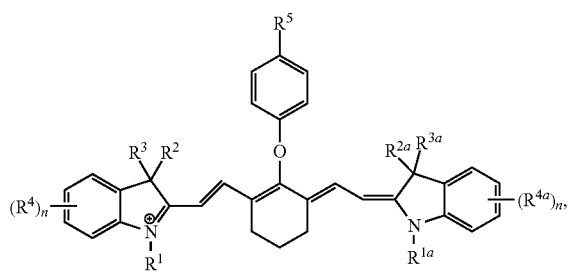

having a purity of at least 75%, wherein
- $R^1$ and $R^{1a}$ are each independently $C_{1-6}$ alkylene-$SO_3H$;
- $R^2$, $R^{2a}$, and $R^3$ are each independently selected from the group consisting of H, $C_{1-6}$ alkyl, and $C_{1-6}$ alkylene-$SO_3H$;
- $R^{3a}$ is $C_{1-6}$ alkylene-COOH;
- each $R^4$ and $R^{4a}$ is independently selected from the group consisting of H, $C_{1-6}$ alkyl, —$SO_3H$, and $C_{1-6}$ alkylene-$SO_3H$;
- $R^5$ is $SO_3H$; and
- each subscript n is an integer from 0 to 4, or salts thereof.

11. The compound of claim 10 having a purity of at least 85%.

12. The compound of claim 10 having a purity of at least 90%.

13. The compound of claim 10 having a purity of at least 95%.

14. The compound of claim 10 having a purity of at least 98%.

15. The compound of claim 10, having the structure:

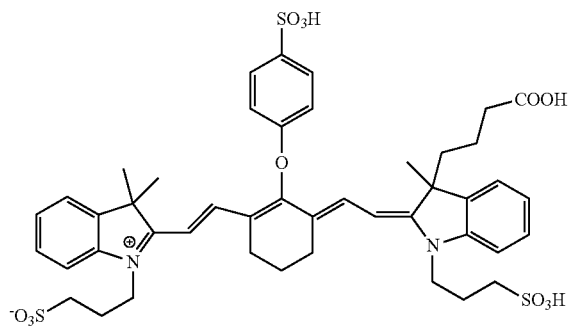

or salts thereof.

16. The compound of claim 10, having the structure:

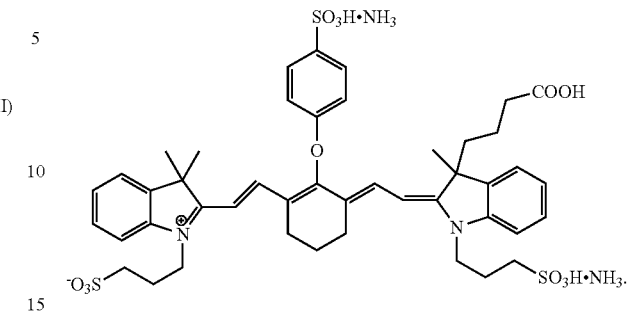

17. The compound of claim 16 having a purity of at least 90%.

18. A compound of Formula VIII having the structure:

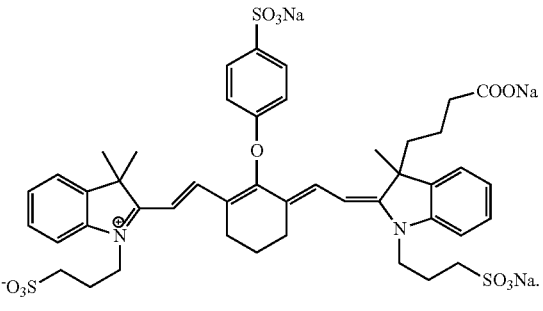

substantially free of the compound having the structure:

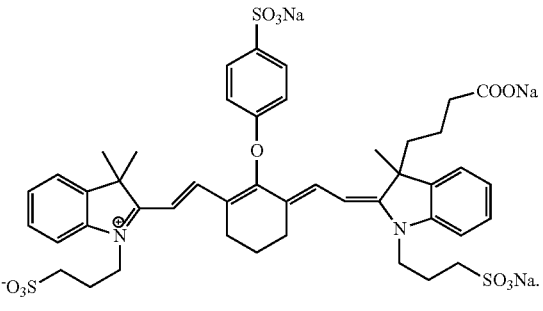

19. The compound of Formula VIII according to claim 18 having a purity of at least 95%.

20. The compound of claim 18, having the structure:
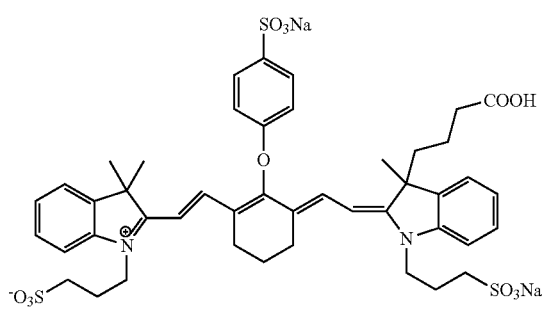
(VIII)
having a purity of at least 95%, substantially free of the compound having the structure:
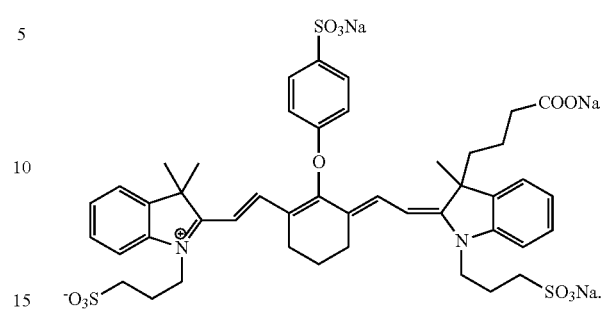
* * * * *